United States Patent [19]

Brot et al.

[11] Patent Number: 4,865,970

[45] Date of Patent: Sep. 12, 1989

[54] METHOD OF DETECTING RIBOSOMAL PROTEIN ANTIBODIES IN SYSTEMIC LUPUS ERYTHEMATOSUS

[75] Inventors: Nathan Brot, Orange, N.J.; Keith Elkon, New York, N.Y.; Susan M. Skelly, Nutley; Herbert Weissbach, Cedar Grove, both of N.J.

[73] Assignees: Hoffmann-La Roche Inc., Nutley, N.J.; Cornell Research Foundation, Inc., Ithaca, N.Y.

[21] Appl. No.: 834,717

[22] Filed: Feb. 28, 1986

[51] Int. Cl.$^4$ .................... G01N 33/53; G01N 3/543; C07K 7/00

[52] U.S. Cl. .................... 435/7; 436/508; 436/518; 436/527; 436/529; 436/811; 530/326; 530/806

[58] Field of Search ............... 435/6, 7; 436/506, 518, 436/538, 523, 527, 529, 804, 809, 811, 508, 804, 824, 543; 530/300, 326, 333, 806

[56] References Cited

U.S. PATENT DOCUMENTS

| | | | |
|---|---|---|---|
| 4,329,331 | 5/1982 | Kallick | 436/506 |
| 4,690,905 | 9/1987 | Diamond | 436/811 |
| 4,692,416 | 9/1987 | Diamond | 436/548 |
| 4,743,538 | 5/1988 | Zabriskie et al. | 435/810 |

FOREIGN PATENT DOCUMENTS

8303473  10/1983  World Int. Prop. O. ............... 435/7

OTHER PUBLICATIONS

Amons et al., Febs Letters, vol. 104, No. 1, Aug. 1979, pp. 85-89.
Meroni et al., Journal of Clinical Immunology, vol. 4, No. 1, 1984, pp. 45-54.
Towbin et al., The Journal of Biological Chemistry, vol. 257, No. 21, 1982, pp. 12709-12715.
Maassen et al., Eur. J. Biochem., vol. 149, Jun. 1985, pp. 609-616.
Koffler et al., Arthritis and Rheumatism, vol. 22, No. 5, May 1979, pp. 463-470.
Gordon et al., The Journal of Rheumatology, vol. 9, No. 2, 1982, pp. 247-252.
Amons et al., Febs Letters, vol. 146, No. 1, Sep. 1982, pp. 143-147.
Francoeur et al., "Identification of Ribosomal Protein Autoantigens", The Journal of Immunology, 1985, 135:2378-2284.
Elkon et al., "Lupus Antoantibodies Target Ribosomal P Proteins", J. Exp. Med., Aug. 1985, 162:459-471.

Primary Examiner—Robert J. Warden
Assistant Examiner—Florina B. Hoffer
Attorney, Agent, or Firm—Jon S. Saxe; George M. Gould; Norman C. Dulak

[57] ABSTRACT

This invention provides methods for the diagnosis of systemic lupus erythematosus in patients, the sera of which contain antibodies reactive against ribosomal proteins P0, P1 and P2. A peptide containing an amino acid sequence corresponding to the carboxyl termini of the ribosomal proteins, which peptide is bound to a solid carrier, is also provided for use in such methods.

7 Claims, No Drawings

METHOD OF DETECTING RIBOSOMAL PROTEIN ANTIBODIES IN SYSTEMIC LUPUS ERYTHEMATOSUS

This invention at least in part was made under NIH Grant No. AM 32845, creating certain rights in this invention in the Federal Government.

BACKGROUND OF THE INVENTION

Systemic lupus erythematosus (SLE) is an autoimmne disease that is characterized primarily by the presence of antibodies against nuclear components. However, about 10–20% of the patients with SLE synthesize antibodies against three ribosomal proteins called P0, P1, and P2. It has been shown that these three proteins contain a common epitope that is recognized by the SLE patients' antibodies. proteins P1 and P2 are thought to be highly conserved in nature and sequencing studies of those proteins isolated from *Artemia salina* show that the carboxyl terminal 22 amino acids of both proteins are identical. There is no homology, however between the amino terminal residues of these proteins.

There is, thus, a need for a reliable and sensitive method of detecting those SLE patients who do not produce antibodies against nuclear components. The present invention is directed to a method of detecting those SLE patients who produce antibodies against ribosomal proteins rather than nuclear components. The method of the invention is, thus, complimentary to existing assays and enables clinicians to detect SLE patients who would not heretofor been detected by existing diagnostic assays.

SUMMARY OF THE INVENTION

The method of the invention is an immunometric assay wherein an antibody to the ribosomal proteins P0, P1 and P2 present in the biological fluid of an SLE patient will bind to a peptide attached to the solid carrier. A labelled antibody binds to the complex formed when the ribosomal protein antibody binds to the immobilized peptide. The amount of labelled antibody associated with the complex is directly proportional to the amount of antibody substance in the fluid sample.

DETAILED DESCRIPTION OF THE INVENTION

The invention is directed to a method for the detection of the presence of an anti-ribosomal protein antibody in a sample of biological fluid, which method comprises the steps of:

(1) binding a peptide having the ability to bind to said anti-ribosomal protein antibody to a solid carrier;

(2) contacting said fluid with said peptide to form an insoluble complex of said peptide and said anti-ribosomal protein antibody;

(3) contacting the complex of Step 2 with a measured amount of labelled anti-human IgG antibody;

(4) separating said solid carrier from said fluid sample and said unreacted labelled antibody: and (5) measuring the amount of labelled antibody associated with said solid carrier:

Wherein the amount cf said label present on said solid-phase substrate is proportional to the quantity of anti-ribosomal protein antibody present in said sample.

As used herein the term "biological fluid" refers to blood, lymph, urine and the like which contains anti-ribosomal protein (P0, P1 or P2) antibodies. Preferred for use herein is serum or plasma, and especially serum containing anti-ribosomal protein antibodies.

As used herein the term "peptide" refers to a peptide which is the functional equivalent of the epitope or antigenic determinant common to the ribosomal proteins, P1, P1 and P2. The epitope is recognized by antibodies produced by 10–20% of the patients suffering from systemic lupus erythematosus.

The peptide of the invention is also referred to herein as "carboxy terminus peptide", "carboxy terminus amino acid fragment" and the like. The preferred peptide for use in the method of the invention has the amino acid sequence:

Lys-Lys-Glu-Glu-Lys-Lys-Glu-Glu-Ser-Glu-Glu-Glu-Asp-Glu-Asp-Met-Gly-Phe-Gly-Leu-Phe-Asp and the pharmaceutically acceptable acid or base addition sals thereof.

The unlabeled carboxy terminus peptide fragment used in the present invention to extract the antibody to P0, P1 or P2 from the sample being tested may be immobilized on any of the common supports used in immunometric assays. Among these may be mentioned filter paper. Plastic beads or test tubes made from polyethylene, polystyrene, polypropylene or other suitable material. Also useful are particulate material such as agarose, crosslinked dextran, and other polysaccharides. The techniques for such bonding are well known to those skilled in the art. For example, antibodies may be bound to polysaccharide polymers using the process described in U.S. Pat. No. 3,645,552.

The labelled anti-human IgG antibody used in the present invention may be provided with the same labels used in prior art immunometric assays. Among these may be mentioned fluorogenic labels for detection by fluorimetry as described in U.S. Pat. No. 3,940,475 and enzymatic markers as described in U.S Pat. No. 3,645,090. It is presently preferred to label the antibody with a radioisotope such as $I^{125}$ using, for example, the procedure of Hunter and Greenwood. Nature 144(1962), page 945 or that of David et al., Biochemistry, Vol 13, pp-1014–1021, 1974.

EXAMPLE 1

Preparation to COOH-Terminal Peptide Fragment

The carboxy terminal peptide fragment used herein was synthesized by solid phase methodology (1) using the BOC/Bzl strategy, and the symmetrical anhydride procedure in a manual shaker. Deprotection and cleavage from the resin were achieved by treatment with anhydrous HF using the modified procedure of Tam et al. (2) The peptide was purified by gel filtration on Sephadex G-25 in 10% acetic acid and high performance liquid chromatography using $\mu$ Bondapack C 18 column in acetonitrile/0.022% trifluroacetic acid system. The purity of the peptide was ascertained by analytical HPLC. amino acid analysis (acid hydroylsis), and microsequencing in a 470A protein sequencer (from Applied Biosystems, Foster City California). The conjugation of the peptide to thyroglobulin was carried out according to the procedure outlined by Chopra et al. (3) The peptide (Peptide No. 1) had the sequence:

Lys-Lys-Glu-Glu-Lys-Lys-Glu-Glu-Ser-Glu-Glu-Glu-Asp-Glu-Asp-Met-Gly-Phe-Gly-Leu-Phe-Asp

The amino terminal peptide (Peptide No. 2) was also made and the peptide had the sequenoe:

Met-Arg-Tyr-Val-Ala-Ala-Tyr-Leu-Leu-Ala-Ala-
Leu-Ser-Gly-Asn-Ala-Asp-Pro-Ser-Thr

The peptides of Example 1 were utilized in the method of the invention using: (1) antibodies from 18 SLE patients that were known to react with proteins P0, P1 and P2; (2) antibodies from 13 SLE patients that did not react with proteins P0, P1 and P2; and (3) antibodies from 20 normal controls. Example 2 provides detailed illustration practice of the method of the invention.

EXAMPLE 2

The thyroglobulin-conjugated peptide was diluted to 4ug/ml with phosphate buffered saline (PBS Buffer) and 50 ul of the solution was added to each well of a Linbro polyvinyl microtiter plate (96 wells per plate). The plates were incubated overnight at 4° C. Thereafter, the plates were washed three times with PBS. Prewarmed (37° C.) Blocking Buffer (PBS+(250 ul) was added to each well of the prewashed plates. The plates were incubated 2 hours at room temperature BSA) and thereafter washed three times with PBS. Thereafter. 50 ul (1:100) of serum sample Were added to each well and the plate was incubated 6 hrs at room temperature. The plate was washed 3× with PBS/Tween buffer (25 mM Sodium Phosphate buffer, 150 mM NaCl, 0.05% Tween 20). To each well 50 ul of $^{125}$I labelled goat anti-human IgG and the plate was incubated 6 hrs at room temperature. The plate was washed with PBS/Tween buffer and then counted in an Packard gamma counter.

All 18 SLE patients with known antibodies to protein P0, P1, and P2 reacted with the C-terminal peptide. Eight of these antibodies were tested against the N-terminal peptide and all failed to react. None of the normal controls or the 13 SLE patients which were known to be non-reactive to P0, P1 or P2 reacted with the carboxyl terminal peptide in the method of the invention. The carboxyl terminal peptide, but not the amino terminal peptide, completely blocks the ability of the SLE antibodies to react with proteins P0, P1, and P2.

THE REFERENCES

1. Barany, G. and Merriefield, R. B. (1980) in the peptides: Analysis, Synthesis, Biology, Eds. Growss, E. and Meienhofer, J. Academic press. New York Vol. 2 pp 1-255.
2. Tam, J. P., Heath, W. F. and Merriefield, R. B. (1983) J. Am. chem. Soc. 105, 6442-6455.
3. Chopra, J. J., Nelsion, J. C., Solomon, D. H. Beall, G. N. J. Clin. Endocrinol. Metab. 32. 299-308 (1971).

What is claimed is:

1. A method for detecting the presence of anti-ribosmal protein antibodies in a boilogical fluid sample from an individual suspected to have systemic lupus erythematosus, which method comprises:
   (a) providing a homogeneous peptide containing an epitope or antigenic detemrinant common to ribosmal proteins P0, P1 and P2 bound to a solid carrier;
   (b) contacting a biolgoical fluid sample suspected to contain anti-robosmal protein antibodies with the bound pepetide to form an insoluble complex of the bound peptide and the antibodies;
   (c) contacting the complex with a known amount of labelled anti-human IgG antibodies to form a complex of the bound peptide, anti-ribosmal protein antibodies and labelled antibodies;
   (d) separating the complex of step c from the fluid sample and unreacted labelled antibodies; and
   (e) measuring the amount of labelled antibodies associated with the separated complex;

wherein the amount of labelled antibody measured is proportional to the quantity of anti-ribosmal protein antibodies present in the sample.

2. The method of claim 1 in which the pepetide has the amino acid sequence:

Lys—Lys—Glu—Glu—Lys—Lys—Glu—Glu—

Ser—Glu—Glu—Glu—Asp—Glu—Asp—

Met—Gly—Phe—Gly—Leu—Phe—Asp—COOH.

3. The method of claim 2 in which the labelled antibody is labelled with a radioisotope, an enzyme or a fluorogenic material.

4. The method of claim 3 in which the label is $^{125}$I.

5. A homogeneous pepetide consisting essentially of the amino acid sequence:

Lys-Lys-Glu-Glu-Lys-Lys-Glu-Glu-Ser-Glu-Glu-
Glu-Asp-Glu-Asp-Met-Gly-Phe-Gly-Leu-Phe-
Asp-COOH or pharmaceutically acceptable acid or base addition salts thereof.

6. The method of claim 3 in which the labelled antibody is labelled with an enzyme.

7. A homogeneous pepitide having the mino acid sequence:

Lys-Lys-Glu,glu-Lys-Lys-Glu-Glu-Ser-Glu-Glu-
Glu-Asp-Glu-Asp-Met-Gly-Phe-Gly-Leu-Phe-
Asp-COOH which peptide is bound to a solid carrier.

* * * * *